United States Patent [19]

Hartmann et al.

[11] Patent Number: 5,053,516

[45] Date of Patent: Oct. 1, 1991

[54] SYNTHESIS OF 2-SUBSTITUTED-5-METHYLPYRIDINES FROM METHYLCYCLOBUTANECARBONITRILE, VALERONITRILE AND PENTENONITRILE INTERMEDIATES

[75] Inventors: Ludwig A. Hartmann, Wilmington, Del.; John F. Stephen, West Chester, Pa.

[73] Assignee: ICI Americas Inc., Wilmington, Del.

[21] Appl. No.: 492,004

[22] Filed: Mar. 12, 1990

Related U.S. Application Data

[63] Continuation of Ser. No. 613,216, May 23, 1984, abandoned.

[51] Int. Cl.$^5$ .................. C07D 213/08; C07D 213/12
[52] U.S. Cl. .................... 546/251; 544/358; 546/230; 558/381
[58] Field of Search ......................... 546/251

[56] References Cited

U.S. PATENT DOCUMENTS

| | | | |
|---|---|---|---|
| 2,342,607 | 7/1944 | Bruson et al. | 260/413 |
| 3,051,622 | 8/1962 | Kuna et al. | 514/162 |
| 4,435,573 | 3/1984 | Lysenko et al. | 546/250 |
| 4,469,896 | 9/1984 | Steiner et al. | 568/495 |
| 4,473,696 | 9/1984 | Hartmann et al. | 546/250 |
| 4,584,380 | 4/1986 | Hartmann et al. | 546/350 |
| 4,658,031 | 4/1987 | Hartmann et al. | 546/193 |
| 4,665,186 | 5/1987 | Steiner et al. | 546/250 |
| 4,709,063 | 11/1987 | Nelson et al. | 549/561 |

FOREIGN PATENT DOCUMENTS 78234  5/1983  European Pat. Off. ......... 558/381

OTHER PUBLICATIONS

Madsen et al.–Tetrahedron, vol. 24, pp. 3369–3379 (1968).
Kolind-Andersen et al.–Bull. Soc. Chim. Belg., vol. 86, pp. 543–550 (1977).
Brannock et al.–Journal of Organic Chemistry, vol. 29, pp. 801–812 (1964).
Chemical Abstracts, vol. 104 (No. 21), Abst. No. 186,315-a, May 26, 1986.

*Primary Examiner*—Alan L. Rotman
*Attorney, Agent, or Firm*—Joel G. Ackerman

[57] ABSTRACT

3-Methyl-2-alkylamino-1-halo-1-cyano cyclobutanes are cleaved under acid conditions to form 2-halo-4-formylvaleronitrile and 4-formyl-2-pentenonitrile which can be cyclized to form 2-substituted-5-methylpyridine derivatives. These pyridine derivatives are useful as starting materials in the manufacture of herbicides such as fluazifop-butyl.

5 Claims, No Drawings

SYNTHESIS OF 2-SUBSTITUTED-5-METHYLPYRIDINES FROM METHYLCYCLOBUTANECARBONITRILE, VALERONITRILE AND PENTENONITRILE INTERMEDIATES

This is a continuation, of application Ser. No. 613,216, filed May 23, 1984 abandoned.

The present invention is directed to the synthesis of novel 3-methyl-2-alkylamino-1-halo-1-cyanocyclobutanes, the synthesis therefrom of 2-halo-4-formylvaleronitrile, and 4-formyl-2-pentenonitrile derivatives and their subsequent use in the synthesis of 2-substituted-5-methylpyridines. In general the process is directed to reacting propionaldehyde, a secondary amine, and a haloacrylonitrile in a stepwise Michael-type addition to form an amino substituted methylcyclobutanecarbonitrile intermediate which is thereafter subjected to acid hydrolysis to form valeronitrile or pentenonitrile derivatives which are thereafter cyclized to form 2-halo or 2-hydroxy-5-methylpyridines.

Various 4-(5-halomethyl-2-pyridyloxy)phenoxy compounds are known to be useful as herbicides as disclosed in European Published Patent Application No. 483, United Kingdom Patent Specifications 1,599,121 and 1,599,126 and U.S. Pat. Nos. 4,184,041 and 4,317,913. For example, butyl 2-[4-(5-trifluoromethyl-2-pyridyloxy)phenoxy]propionate which is also known as fluazifop-butyl is an effective grass herbicide which can be used in fields where broad leaved crops such as cotton and soybeans are cultivated. Important starting materials for such pyridyloxyphenoxy compounds are the 2-halo-5-trichloromethylpyridines such as 2-chloro-5-trichloromethylpyridine described in U.S. Pat. No. 4,317,913. Such 2-halo-5-trichloromethylpyridines in turn may be prepared by chlorinating under ultraviolet light irradiation a 2-halo-5-methylpyridine as described in U.S. Pat. No. 4,152,328.

An object of the present invention is to provide an efficient economical and reliable synthesis of 2-substituted-5-methylpyridines as well as for certain intermediates useful in their synthesis. It is another object to provide novel intermediates for use in manufacturing the 2-substituted-5-methylpyridines such as 1-halo-2-alkylamino-3-methyl-cyclobutanecarbonitrile, 2-halo-4-formylvaleronitrile, and 4-formyl-2-pentenonitrile.

A further object of the present invention is to provide for a method for preparing 2-halo-5-methylpyridines without utilizing pyridine or 3-picoline starting materials thus avoiding the problems of by-product formation in the halogenation reaction.

Still another object is to provide an alternate process to that presented in our pending application U.S. Ser. No. 433,273 filed Oct. 7, 1982.

The present invention comprises a method for the synthesis of a 5-methylpyridine derivative of the formula (I):

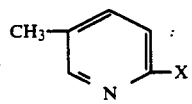
(I)

wherein X is a halogen or hydroxyl group by cyclization in the presence of an acid catalyst of novel compounds having the formula (II) or formula (III):

$$OCHCH(CH_3)CH_2CH(X)CN \quad (II)$$

$$OCHCH(CH_3)CH=CHCN \quad (III)$$

which are made by acidic hydrolysis under mild conditions (formula II) or stronger conditions (formula III) of a novel cyclobutane derivative having a general formula (IV):

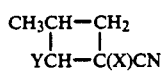
(IV)

wherein Y is $-NR^1R^2$ wherein $R^1$ and $R^2$ are selected from individual substituted and unsubstituted alkyl groups having 1–6 carbon atoms and groups connected to form 5- or 6-membered heterocyclic rings and wherein X is chlorine or bromine.

Preparation of Methylcyclobutane Carbonitrile Derivatives

Compounds of the general formula (IV) are made by condensing propionaldehyde in a Michael-type 2-step addition with an acrylic compound of the following formula (V):

$$CH_2=C(X)CN \quad (V)$$

The Michael addition may be conducted as known in the art such as at a temperature of about 0° to 100° C. neat or in the presence of an inert solvent and optionally in the presence of a base catalyst. The compound of formula (IV) may be recovered by extraction, chromatography or distillation. Preferably the Michael addition is carried out in two steps by first reacting the propionaldehyde with a secondary amine of the formula $HNR^1R^2$ wherein $R^1$ and $R^2$ are independently organic moieties which may be attached to each other to form a ring, to form directly or through an intermediate aminal of formula (VI) an enamine having a structure (VII)

$$CH_3-CH_2-CYY \quad (VI)$$

or $$CH_3-CH=CHY \quad (VII)$$

and mixtures thereof wherein Y is $-NR^1R^2$. In particular $R^1$ and $R^2$ include individual substituted and unsubstituted alkyl of about 1–6 carbon atoms such as methyl, ethyl, propyl and butyl and pentyl and, $R^1$ and $R^2$ are connected substituted and unsubstituted heterocyclic rings such as 5- or 6-membered heterocyclic rings for example to define the secondary amine such as pyrrolidine, piperidine and morpholine. This reaction may be conducted at about −10° to 35° C. preferably in the presence of an alkali or alkali earth metal carbonate, sulfate, halide or oxide for example calcium sulfate, magnesium sulfate, calcium chloride, sodium sulfate, magnesium oxide, potassium carbonate, calcium oxide or even molecular sieves as disclosed by D. Roelofsen et al. in Recueil, Vol. 91, pages 605–610 (1972) with at least 2 moles of secondary amine per mol of propionaldehyde. The secondary amine must be used in excess in view of the formation of an aminal of the formula $CH_3CH_2CH(NR^1R^2)_2$ which is formed in addition to the enamine of the formula $CH_3CH=CH(NR^1R^2)$. The aminal and enamine mixture in mol ratios of 1:1 and 1:6 usually occurs as a liquid which may be heated to distill unreacted secondary amine and thereafter combined with a solvent such as acetonitrile and reacted with α-haloacrylonitrile under mild conditions to form the cyclobutane derivative of formula (IV). The synthesis of cyclobutanes of this type is described in detail by I. Fleming et al. in the Journal of the Chemical Society, pages 2165-2174 (1964) and U.S. Pat. Nos. 3,051,622: 3,133,924: 3,369,024: 3,481,936 and 3,481,939. The 1-chloro-2-(4-morpholino)-3-ethylcyclobutane carbonitrile homolog has been made by Madsen and Lawessen, Tetrahedron, 24, 3369 (1968) by the addition of α-chloroacrylonitrile to morpholinobutene in acetonitrile solvent. While the reaction may be carried out neat it is preferred to carry it out in the presence of a solvent such as an ether, ester, halogenated alkane, ketone or nitrile solvent for example acetonitrile. The reaction may be carried out at room temperature up to the boiling point of the haloacrylic compound for example up to about 120° C. with the higher temperature of this range being advantageously used to complete the reaction. Satisfactory yields are obtained at temperatures of 25°-80° C. In carrying out the reaction it is preferred that the aminal/enamine mixture be cooled to −5° to 20° C. with dropwise addition of the haloacrylonitrile followed by warming to the range of room temperature to about the boiling of the halonitrile solvent.

The α-haloacrylonitriles of formula (V) are known and made by halogenation of acrylonitrile to form the 2,3-dihalopropionitrile followed by dehydrohalogenation.

Preparation of 2-Halo-4-formylvaleronitrile

The compounds of formula (II) are made by hydrolyzing to cleave cyclobutanes of formula (IV) with recovery of the secondary amine $HNR^1R^2$. The reaction may be conducted in an aqueous acidic medium such as in the presence of an aqueous acid such as acetic, sulfuric, hydrochloric, phosphoric or p-toluene sulfonic acid optionally in a solvent such as a nitrile, ether, ester, halogenated alkane or ketone. A solvent system is preferred which allows the hydrolysis product to separate as a water insoluble layer during the reaction. The hydrolysis is carried out under controlled conditions at a temperature of about 25° to 80° C. at a pH of about 1.5 to 4.5. A solvent other than the aqueous acidic reaction medium need not be present. Aldehydes of formula (II) may be recovered by phase separation and extraction of the aqueous acid solution containing the secondary amine with a neutral organic solvent such as ethyl acetate or methylene chloride.

Preparation of 4-Formyl-2-Pentenonitrile

In the preparation of the material of formula (II) as described above a minor amount of a dehydrohalogenated product is formed as formula (III). However, if the material of formula (IV) is heated at 80°-105° C. especially in the presence of aqueous organic acid the product of formula (III) is obtained directly.

Preparation of 2-Halo-5-Methylpyridine

The aldehydes of formula (II) or (III) are converted directly to the pyridine of formula (I) (when X=Cl) by acid catalyzed ring closure. For example, the compound of formula (II) may be cyclized with hydrogen halide such as HCl, and sulfuric acid, phosphoric acid or sulfonic acid at a temperature of 25° to about 100° C. neat or in a solvent such as halogenated hydrocarbon or dimethyl formamide. Similar ring closures and reaction conditions are described in. U.S. Pat. No. 4,245,098 and Europat Pub. No. 46735 (Mar. 3, 1982). The preparation of 2,3,5-trichloropyridine from 2,4,4-trichloro-4-formylbutyronitrile is disclosed in these references.

In the case with the material of formula (III) the acid catalyzed ring closure is carried out with either hydrogen bromide or hydrogen chloride depending upon the halide intended.

Preparation of 2-Hydroxy-5-Methylpyridine

When the compounds of formula (II) and (III) are heated in the presence of p-toluene sulfonic acid or other strong organic acids or mineral acids at temperatures of 110°-135° C., 2-hydroxy-5-methylpyridine is formed in high yields.

N. P. Susherina et al. in Chemical Abstracts, Vol. 55, page 7410e, and A. I. Meyers in J. Organic Chemistry, Vol. 29, page 1435-1438 (1964) and U.S. Pat. No. 3,944,559 disclose ring closures of α-ketonitriles and of 2-(2-cyanoalkyl)cyclohexanones and the preparation of certain 3,4-dihydro-2-pyridones and 2-pyridones.

In the following examples and throughout the specification the following abbreviations are used: ° C. (degrees centigrade): ml (millileters): g (grams): m (mols): mm (millimeters): GLC (gas liquid chromatography); GC/MS (gas chromatograph-mass spectrometry): IR (infra red); NMR (nuclear magnetic resonance): mp (melting point); bp (boiling point): DSC (differential scanning calorimetry): MS (mass spectrometry): and the conventional symbols for the chemical elements. All proportions expressed herein are parts by weight unless otherwise specified.

Preparation A

Preparation of 1-(N-morpholino)prop-1-ene (MP) and 1,1-bis(N-morpholino)propane(aminal)

A slurry was prepared from 200 g distilled morpholine and 4.25 g anhydrous potassium carbonate. This slurry was cooled to 25° C. and stirred while propionaldehyde (61.9 g) was added dropwise. The temperature was held at 25° by cooling with an ice-bath during the addition (40 minutes). Reaction was continued at 25°-30° C. for 2 hours prior to vacuum stripping at 30°-50° C. under moderate vacuum (20-40 mm). The product (aminal) was filtered and was then subjected to thermal cracking under vacuum, using an efficient fractionating column to avoid losses of aminal or morpholino-propene. Cracking to morpholinopropene was carried out for about 2 hours at a pot temperature of 65°-85° C. with the reflux adjusted so that a still-head temperature of about 50° C./40 mm could be maintained. The product was a light-colored liquid of low viscosity, weighing 89.1 g. The mol ratio of MP to aminal, as determined by NMR analysis, was 2.5:1 (this corresponds to about 60% MP/40% aminal in weight percent).

Preparation B

Preparation of 1-(N-morpholino)prop-1-ene (MP) and 1,1-bis-(morpholino)propane(aminal)

A slurry of 200 g morpholine and 0.85 g anhydrous potassium carbonate was treated with 61.9 g propionaldehyde as in Example 1. Partial cracking to MP was carried out for about 1 hour at 80° C. pot temperature and the product composition then corresponded to about 2:1 MP:aminal. One half of the product (63.6 g)

was cracked further for one hour at 82°-89° C. pot temperature and 40 mm Hg vacuum, with the still-head temperature at 45°-51° C. The yield of product was 40.8 g and the composition (mol ratio) by NMR analysis was 5:1 MP:aminal (weight percent: 75% MP/25% aminal).

Example 1

Preparation of 1-Chloro-2-(4-morpholino)-3-methylcyclobutane Carbonitrile

A 50.6 g portion of the material made in Preparation A was diluted with 50 ml acetonitrile and treated gradually with a solution of 41.2 g of α-chloroacrylonitrile in 40 ml of acetonitrile over a period of 1.5 hours at 25° C. The product was heated at 50° C. for 3 hours and was then stripped at 50° C. under moderate low pressure (150 mm-40 mm). The product residue weighed 90.4 g. It was chilled at 0° C. and crystallized. A slurry with one part hexane was filtered to obtain 33.2 g pure product (mp 77°-78° C.). Analysis: C, 55.57: H, 7.09; N, 12.95: Cl, 16.34. Calculated: C, 55.95: H, 7.04; N, 13.04: Cl, 16.51. The product was purified by recrystallization from a mixture of toluene and hexane (1 part sample, 1 part toluene, 2 parts hexane (mp 84°-85° C.). NMR analysis showed that the cyclobutane product was obtained.

Example 2

Preparation of 1-Bromo-2-(4-morpholino)-3-methylcyclobutane Carbonitrile

A 50 g portion of the MP-aminal product of Preparation B, is diluted with 50 ml acetonitrile and treated gradually with a solution of 60 g (α-bromoacrylonitrile in 60 ml acetonitrile at 25° C. (1.5 hours). The product is heated at 50° C. for 3 hours and is then vacuum stripped at 50° C. under moderate vacuum (expected yield = 110 g). The product may be crystallized upon cooling and recovered as a solid after filtration. It may be recrystallized from hexane/acetonitrile.

Example 3

Preparation of 2-Chloro-4-formylvaleronitrile 12 g of the product of Example 1 having mp of 77°-78° C. and 7.2 ml acetonitrile was stirred and treated with 7.2 ml 8N H2SO4 at room temperature in portions until all was dissolved. This reaction mixture was then heated to 60° and held at that temperature for 2 hours. The product mixture was separated in a separatory funnel. The upper product layer (12.0 g) was purified by adding 25 ml toluene and washing twice with 8 ml water. The solvent was then vacuum stripped at 55° C./30 mm and 6.7 g of product was obtained as residue. The content of the valeronitrile derivative was 94% as determined by GLC. Analysis: C, 48.45; H, 5.65: Cl, 22.40: N, 10.52. Calculated: C, 49.5: H, 5.53; Cl, 24.35; N, 9.62. The structure was confirmed by GC/MS. The product was further purified by distillation at vapor temperature 92°-95° C./4 mm Hg and was obtained as a colorless non-viscous liquid.

Example 4

Preparation of 2-Bromo-4-formylvaleronitrile

A mixture of 50 g cyclobutane carbonitrile product of Example 2 and 30 ml acetonitrile is treated at room temperature with 25 ml 8N H2SO4 in portions until all is dissolved. The hydrolysis is then completed at 60° C. (2 hours). The upper layer (product) is separated and purified by adding 75 ml toluene and washing several times with 20 ml water. The solvent is then vacuum-stripped at 55° C./30 mm and 2-bromo-4-formylvaleronitrile is obtained as a liquid residue.

Example 5

Synthesis of 2-Chloro-4-formylvaleronitrile

A sample of 40.1 g non-crystalline cyclobutanecarbonitrile derivative, obtained as hexane-insoluble product (lower layer) after crystallization and filtration (Example 1), was treated with 24 ml 8N H2SO4, dropwise at 28°-34° C. while stirring and cooling. The reaction mixture was heated at 62°-64° C. for 1 hour and the 2-phase reaction product was then separated. 2-Chloro-4-formylvaleronitrile was isolated as the upper layer. The yield was 14.7 g; GLC analysis showed that the product was predominantly 2-chloro-4-formylvaleronitrile with a small amount of 4-formyl-2-pentenonitrile also present.

Example 6

Synthesis of 4-Formyl-2-pentenonitrile

A sample of 5 g crystallized cyclobutanecarbonitrile product (Example 1) was mixed with 10 ml glacial acetic acid and 10 ml water. The reaction mixture was stirred and heated at 80° C. for 20 minutes and was then vacuum stripped at 100° C./20 mm after a period of 16 hours at room temperature. The product residue was diluted with 18 g toluene and residual aqueous phase was separated. The toluene solution of product was washed two times with 5 ml H2O and vacuum stripped at 50° C./20 mm. The yield of product was 1.1 g. The product was predominantly 4-formyl-2-pentenonitrile by GLC (N, 12.6%: calc.: N, 12.8%: residual Cl, 3%).

Example 7

Preparation of 2-Chloro-5-methylpyridine

A 2 g sample of undistilled product from Example 3 was dissolved in 8 g dimethyl formamide. This solution was stirred while HCl gas was introduced very slowly as the temperature was raised to 60° C. The temperature was held at 60°-85° C. for 1 hour and then at 100° C. for 7 hours while HCl was introduced slowly throughout. An additional 3 g of dimethyl formamide was added after 3 hours at 100° C. A total of 6.3 g of HCl was picked up by the mixture during the reaction. Product was worked up by dissolving in 50 ml water and 20 ml of acetonitrile and neutralizing to a pH of 8.4 with 11 g solid sodium carbonate. The 2-chloro-5-methylpyridine product was extracted into 3 portions each of 25 ml toluene and combined and thereafter washed 3 times with 15 ml portions water. The toluene solution was vacuum stripped at 50° C. and 25 mm. 1.2 g of 2-chloro-5-methylpyridine was recovered as a mobile liquid. It was identified by GLC and GC/MS.

Example 8

Preparation of 2-Hydroxy-5-methylpyridine

A 0.5 g portion of the product of Example 3 was mixed with 0.03 g p-toluenesulfonic acid and stirred for 2 hours while heat was applied by immersing in an oil bath at 110°-130° C. Hydrogen chloride gas was given off.

This product was diluted with 50% aqueous ethanol, neutralized with sodium carbonate and analyzed by GLC. The yield of 2-hydroxy-5-methylpyridine was 0.25 g (67%) when compared with pure material. The product was isolated and characterized as follows: The neutralized solution of reaction product was vacuum stripped to dryness. The residue was treated with 2 mls ethanol and filtered. The filtrate was treated with activated carbon (Darco® G-60) heated to boiling and filtered. Vacuum stripping yielded 0.29 g. This material was characterized as predominantly 2-hydroxy-5-methylpyridine by GLC analysis. This product was then stirred with 0.5 ml acetone and recrystallized at room temperature and 0° C. and filtered. The product was washed 3 times with 0.5 mls acetone. The washed product was 99.9% 2-hydroxy-5-methylpyridine, as determined by DSC analysis, with a melting point of 164° C. Analysis by MS matched an authentic sample.

Example 9

Preparation of 2-Chloro-5-methylpyridine

A solution containing 0.6 g of the product of Example 6 dissolved in dimethylformamide was treated with a slow stream of hydrogen chloride gas at 35°-70° C. until the exothermic reaction terminated. HCl gas addition was continued at 80° C. for 1.5 hours, then at 100° C. for 3 hours. Pick-up of HCl amounted to 1.8 g. The product was diluted with 6 parts of a 1:1 mixture of water and acetonitrile and neutralized to a pH 8.5 with sodium carbonate. This material was extracted with five 3 part portions of toluene. The toluene solution was analyzed by GLC and contained only 2-chloro-5-methylpyridine which indicated an essentially quantitative yield.

Example 10

Preparation of 2-Hydroxy-5-methylpyridine

A 0.5 g portion of the product of Example 6 was mixed with 0.03 gm p-toluenesulfonic acid and stirred under nitrogen at 130°-135° C. GLC analysis indicated the product to be predominately 2-hydroxy-5-methylpyridine.

What is claimed is:

1. A process for synthesizing a 2-halo-5-methylpyridine wherein said halo group is selected from Br and Cl which comprises cyclizing 4-formyl-2-pentenonitrile in the presence of HBr or HCl at temperatures gradually increasing from 35°-100° C.

2. A process for synthesizing 2-hydroxy-5-methylpyridine which comprises heating 4-formyl-2-pentenonitrile in the presence of a sulfonic acid.

3. A process of claim 2 wherein said sulfonic acid is p-toluenesulfonic acid.

4. A method for producing a 5-methylpyridine compound having the formula

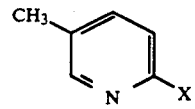

in which X is halogen or hydroxyl comprising:
(a) reacting propionaldehyde in a Michael addition with an acrylic compound having the formula

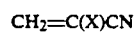

CH$_2$=C(X)CN to produce a cyclobutane derivative having the formula

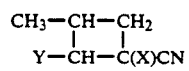

in which Y is NR$^1$R$^2$ and R$^1$ and R$^2$ are each optionally substituted C$_1$-C$_6$ alkyl groups, or R$^1$ and R$^2$ together with the nitrogen atom form a 5- or 6-membered heterocyclic ring;
(b) subjecting the cyclobutane derivative to acid hydrolysis so as to produce a nitrile having the formula

OCHCH(CH$_3$)CH$_2$CH(X)CN or

OCHCH(CH$_3$)CH=CHCN;

and
(c) cyclizing the nitrile of step (b) in the presence of an acid catalyst.

5. A process according to claim 4 in which step (a) is carried out by:
(i) reacting propionaldehyde with an amine having the formula HNR$^1$R$^2$ in which R$^1$ and R$^2$ are each optionally substituted C$_1$-C$_6$ alkyl groups, or R$^1$ and R$^2$ together with the nitrogen atom form a 5- or 6-membered heterocyclic ring to produce an enamine having the formula CH$_3$—CH=CHY in which Y is NR$^1$R$^2$; and
(ii) reacting the enamine of step (i) with an α-haloacrylonitrile to form the cyclobutane derivative.

* * * * *